US012736514B2

(12) United States Patent
Yang et al.

(10) Patent No.: US 12,736,514 B2
(45) Date of Patent: Sep. 15, 2026

(54) RESERVOIR AREA WATER BLOOM RAPID MONITORING METHOD AND DEVICE BASED ON UNMANNED AERIAL VEHICLE SWARM COORDINATION

(71) Applicants: HUANENG LANCANG RIVER HYDROPOWER INC., Kunming (CN); HOHAI UNIVERSITY, Nanjing (CN)

(72) Inventors: Zuobin Yang, Kunming (CN); Wei Zeng, Kunming (CN); Jiaxing Yang, Kunming (CN); Liang Shi, Kunming (CN); Hao Chen, Kunming (CN); Rongzhi Qi, Kunming (CN); Honggang Chen, Kunming (CN); Shiqi Wang, Kunming (CN); Haotian Zheng, Kunming (CN); Yuhai Ren, Kunming (CN); Jinjie Li, Kunming (CN); Huiqing Dao, Kunming (CN); Zhongjun Wang, Kunming (CN); Juqiang Gan, Kunming (CN); Lihua Guo, Kunming (CN); Jingguan Li, Kunming (CN); Xingyong Liu, Kunming (CN); Wan Zhang, Kunming (CN); Zengfu Wang, Kunming (CN); Wenhui Yang, Kunming (CN)

(73) Assignee: Huaneng Lancang River Hydropower Inc., Kunming (CN)

( * ) Notice: Subject to any disclaimer, the term of this patent is extended or adjusted under 35 U.S.C. 154(b) by 227 days.

(21) Appl. No.: 18/885,682

(22) Filed: Sep. 15, 2024

(65) Prior Publication Data

US 2025/0347673 A1 Nov. 13, 2025

(30) Foreign Application Priority Data

May 7, 2024 (CN) ........................ 202410553610.8

(51) Int. Cl.
*G06V 20/17* (2022.01)
*G01N 33/18* (2006.01)
(Continued)

(52) U.S. Cl.
CPC .......... *G01N 33/1866* (2013.01); *G05D 1/69* (2024.01); *G06V 10/82* (2022.01); *G06V 20/17* (2022.01);
(Continued)

(58) Field of Classification Search
CPC .... G01N 33/1866; G06V 20/17; G06V 10/82; G05D 1/69; G05D 2109/20;
(Continued)

(56) References Cited

U.S. PATENT DOCUMENTS 12,129,191 B1 * 10/2024 Narayanan ................ C02F 1/50
2023/0386183 A1 * 11/2023 Li ........................ G06V 10/774

FOREIGN PATENT DOCUMENTS

CN 116610958 A * 8/2023 .......... G06F 18/214
CN 116778363 A * 9/2023

OTHER PUBLICATIONS

Vivaldini, Multi-UAV Collaborative System for the Identification of Surface Cyanobacterial Blooms and Aquatic Macrophytes, Feb. 23, 2024, Springer, Journal of Intelligent Robotics, vol. 110 (Year: 2024).*

(Continued)

*Primary Examiner* — Matthias S Weisfeld
(74) *Attorney, Agent, or Firm* — Ming Jiang; OPENPTO US LLC

(57) ABSTRACT

A reservoir area water bloom rapid monitoring method and a device based on unmanned aerial vehicle swarm coordination are provided. Through the local updating quantification technology, the communication volume between UAV and central server is compressed and the communication (Continued)

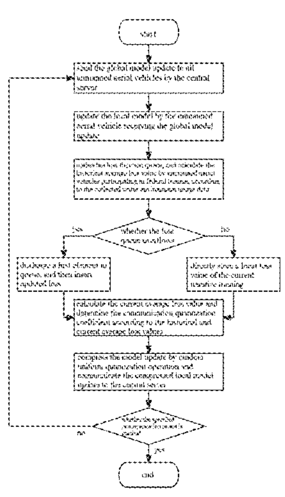

efficiency of federated learning is optimized on the premise of ensuring the accuracy of the reservoir area water bloom monitoring model. The local update quantification defines the loss function queue for UAV, and uses the ratio of historical and current loss functions to reasonably quantify the upstream model update. According to the disclosure, the problems that pictures collected by unmanned aerial vehicle swarm are difficult to upload in large quantities, the communication volume required for reservoir area water bloom monitoring is too large, and the reservoir area water bloom monitoring model converges slowly due to frequent communication are solved.

13 Claims, 1 Drawing Sheet

(51) Int. Cl.

| | |
|---|---|
| ***G05D 1/69*** | (2024.01) |
| ***G06V 10/82*** | (2022.01) |
| *G05D 101/15* | (2024.01) |
| *G05D 105/80* | (2024.01) |
| *G05D 107/00* | (2024.01) |
| *G05D 109/20* | (2024.01) |
| *G05D 111/10* | (2024.01) |
| *G05D 111/30* | (2024.01) |

(52) U.S. Cl.
CPC ..... *G05D 2101/15* (2024.01); *G05D 2105/80* (2024.01); *G05D 2107/25* (2024.01); *G05D 2109/20* (2024.01); *G05D 2111/10* (2024.01); *G05D 2111/32* (2024.01)

(58) Field of Classification Search
CPC ........... G05D 2101/15; G05D 2105/80; G05D 2107/25; G05D 2111/32; G05D 2111/10
USPC .............................................................. 701/1
See application file for complete search history.

(56) References Cited

OTHER PUBLICATIONS

Kislik, UAVs in Support of Algal Bloom Research: A Review of Current Applications and Future Opportunities, Oct. 17, 2018, MDPI, drones (Year: 2018).*

Cheng, Remote sensing of coastal algal blooms using unmanned aerial vehicles (UAVs), Mar. 2020, ScienceDirect, Marine Pollution, vol. 152 (Year: 2020).*

* cited by examiner

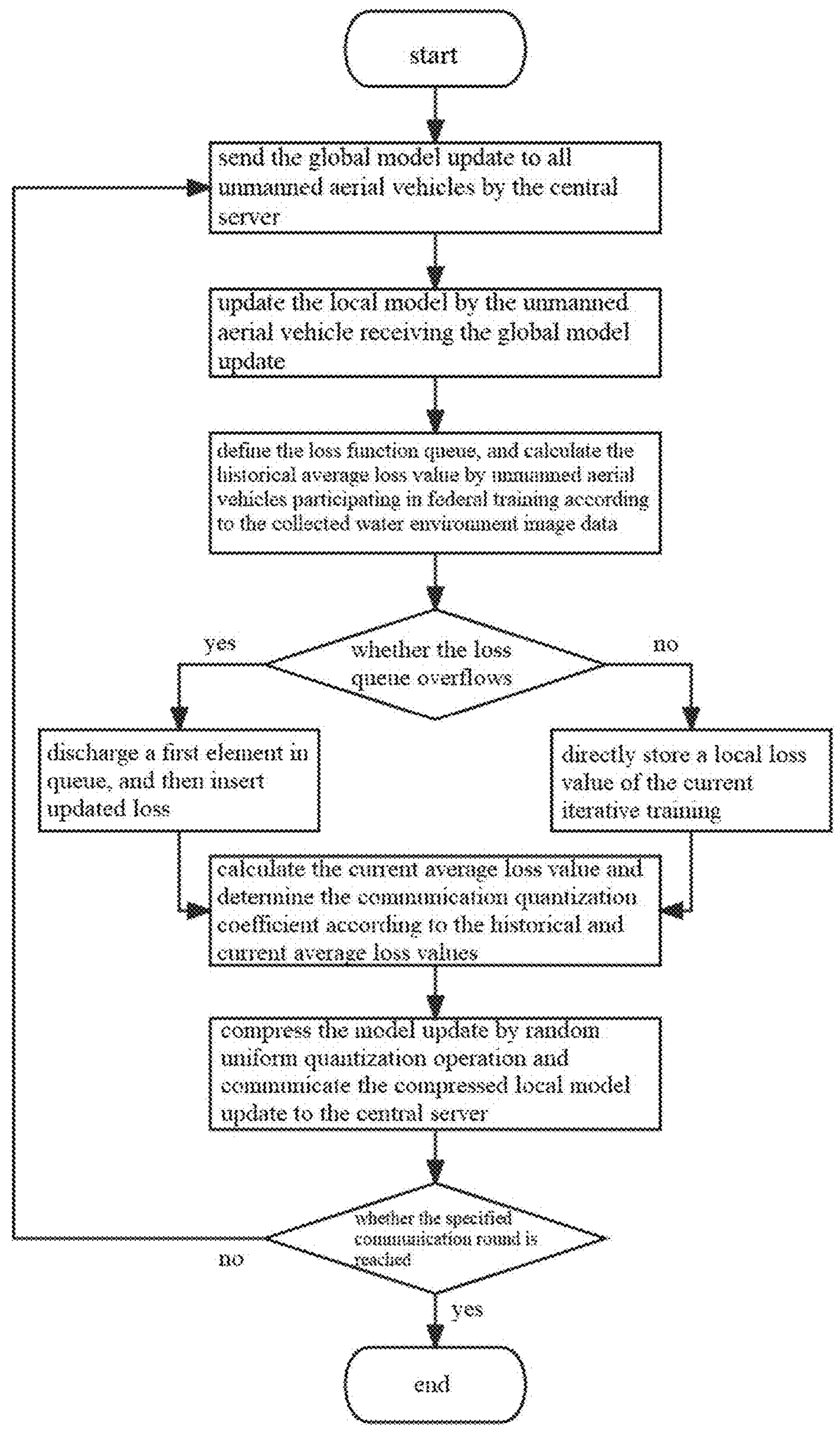
start
send the global model update to all unmanned aerial vehicles by the central server
update the local model by the unmanned aerial vehicle receiving the global model update
define the loss function queue, and calculate the historical average loss value by unmanned aerial vehicles participating in federal training according to the collected water environment image data
whether the loss queue overflows
yes
no
discharge a first element in queue, and then insert updated loss
directly store a local loss value of the current iterative training
calculate the current average loss value and determine the communication quantization coefficient according to the historical and current average loss values
compress the model update by random uniform quantization operation and communicate the compressed local model update to the central server
whether the specified communication round is reached
no
yes
end

RESERVOIR AREA WATER BLOOM RAPID MONITORING METHOD AND DEVICE BASED ON UNMANNED AERIAL VEHICLE SWARM COORDINATION

CROSS-REFERENCE OF RELATED APPLICATION

This application claims priority of Chinese Patent Application No. 202410553610.8, filed on May 7, 2024, the content of which is hereby incorporated by reference.

TECHNICAL FIELD

The disclosure relates to a reservoir area water bloom rapid monitoring method and device based on unmanned aerial vehicle swarm coordination, and belongs to the technical field of image recognition and classification.

BACKGROUND

With the rapid progress of science and technology, the traditional Internet is gradually evolving into an intelligent Internet of Things. Intelligent Internet of Things collects a large amount of data through edge devices (such as smart phones, wireless cameras, unmanned aerial vehicles, Internet of Things sensors, etc.), and provides users with intelligent application services through distributed training of complex network models. The data quality and quantity of edge devices directly affect the performance of intelligent applications. In order to provide efficient intelligent application services, it is very important to obtain reliable and sufficient data. However, in reality, due to industry competition and cumbersome administrative procedures, data are scattered among different organizations. At the same time, the integration of scattered data faces huge costs, and may even be restricted by law, resulting in the data missing when training models. Data missing will damage the accuracy of the model. In order to make rational use of isolated data, protect user data security and improve the accuracy of intelligent application model, federated learning is often used to provide edge intelligent application services. Federated learning uses the local data set of the client to train local models, then aggregates these local models to the server to generate global models, and then sends the global models to the client for the next round of training. The whole training process continues until the global model meets the established requirements, that is, it reaches the preset performance index or preset time. Different from traditional distributed learning, federated learning always stores data locally, which can guarantee data privacy to the greatest extent.

UAV equipped with specific sensors can effectively monitor water quality, especially the monitoring of algae. At the same time, it can also detect oil pollution and other pollutants floating on the water surface, and realize monitoring and warning functions by identifying risk sources, such as oil pollution leaked by manual operation or ships. In the monitoring of reservoir area water bloom, because of the special geographical location of the reservoir area, the image and video data needed for water bloom monitoring are usually collected by unmanned aerial vehicle (UAV) swarm, which is private. These data are difficult to train the water bloom monitoring model by the traditional centralized machine learning method, because the privacy of the data needs to be fully protected. Federated learning technology can effectively avoid the risk of data leakage during transmission. However, due to the huge amount of data collected by the UAV swarm, using federated learning to train the water bloom monitoring model will produce a huge communication cost. Under the condition of low network bandwidth, frequent communication may lead to data packets being blocked in the network and unable to be transmitted to the destination on time, resulting in network delay or data loss, thus reducing the convergence speed of the global model

SUMMARY

The purpose of the disclosure is to solve the problem that the convergence speed of the reservoir area water bloom monitoring model is slow due to the communication cost in federated learning. Based on the local updating quantification technology, the disclosure provides a reservoir area water bloom rapid monitoring method and device based on unmanned aerial vehicle swarm coordination, which can greatly reduce the communication cost of federated learning on the basis of ensuring the accuracy of the global model, accelerate the convergence speed of the reservoir area water bloom monitoring model, and greatly reduce the communication volume in the training process of the reservoir area water bloom monitoring model.

The technical scheme is as follows: the reservoir area water bloom rapid monitoring method based on the unmanned aerial vehicle swarm coordination compresses the model update between UAVs and a central server through the local update quantification technology, fully considers the heterogeneity of data distribution, and minimizes the communication volume transmitted in a single communication round on the premise of ensuring the accuracy of the reservoir area water bloom monitoring model, thereby optimizing the communication efficiency of federal learning.

The local update quantification defines the loss function queue for the UAV, and uses the ratio of historical and current loss functions to reasonably quantify the upstream model update.

A reservoir area water bloom rapid monitoring method based on unmanned aerial vehicle swarm coordination collects reservoir area water bloom image data by unmanned aerial vehicle swarm, and obtains a global model by aggregating a local model trained on unmanned aerial vehicles, that is a reservoir area water bloom rapid monitoring model. The method includes following steps:

S1: according to water bloom image data taken by the unmanned aerial vehicles, training the local model by the unmanned aerial vehicles through federal learning algorithm, the local model is the reservoir area water bloom rapid monitoring model; in a training process of r-th round, updating r−1th round trained global model $\Delta\tilde{w}^{r-1}$ and sending to N unmanned aerial vehicles by the central server;

S2: updating the local model to $$w_i^r = w_i^{r-1} + \Delta\tilde{w}^{r-1}$$

by the N unmanned aerial vehicles receiving global model update $\Delta\tilde{w}^{r-1}$, where $$w_i^r$$

is a local model after updating $\Delta\tilde{w}^{r-1}$ and $$w_i^{r-1}$$

is a local model before updating $\Delta\tilde{w}^{r-1}$;

S3: after updating the local model, defining a loss function queue according to the water bloom image data collected by unmanned aerial vehicles participating in federal training, and calculating a historical average loss value and a current average loss value;

S4: determining a communication quantization coefficient for the local model by using a ratio of a historical loss function to a current loss function, and further introducing a fading learning rate to improve a problem of quantization effect gradually weakening with communication round iteration;

S5: compressing local model update $\Delta\tilde{w}_i$ by random and uniform quantization operation, where $\Delta\tilde{w}_i$ is quantized local model update of unmanned aerial vehicle $c_i$; transmitting and communicating $\Delta\tilde{w}_i$ to the central server; continuing communication between the central server and the UAV swarm, iteratively updating the local model of the UAV and the global model of the central server, and repeating S1-S5 until the global model converges or reaches a specified communication round, greatly reducing federal learning communication cost on a basis of ensuring accuracy of the global model, accelerating convergence speed of the reservoir area water bloom monitoring model, and greatly reducing communication volume in a training process of the reservoir area water bloom monitoring model, where a final obtained global model is the reservoir area water bloom rapid monitoring model.

Further, specific steps of calculating the historical average loss value and the current average loss value in the S3 are as follows:

defining an empty queue $\text{Queue}_i$ with a length of $\mu$ by each of the unmanned aerial vehicles, so as to store at most $\mu$ loss function values during local calculation of unmanned aerial vehicle $c_i$;

then, calculating the historical average loss value by the unmanned aerial vehicles; where the historical average loss value refers to average loss stored in queue when the unmanned aerial vehicles fail to calculate current local loss:

$$l_{history} = \text{sum}(\text{Queue}_i)/\text{len}(\text{Queue}_i)$$

where $\text{sum}(\text{Queue}_i)$ is sum of loss values stored in queue of unmanned aerial vehicle $c_i$, and $\text{len}(\text{Queue}_i)$ is a queue length of $c_i$;

after the unmanned aerial vehicles obtain the historical average loss value $l_{history}$, calculating local loss of current iterative training by the unmanned aerial vehicle $c_i$ and storing in training loss queue $\text{Queue}_i$; where before storing in the training loss queue, judging whether the training loss queue overflows, that is, whether a length of the training loss queue is equal to $\mu$; if equal, discharging a first element in the training loss queue, and then inserting updated loss; if not equal, directly storing a local loss value of the current iterative training;

after updating the loss queue, obtaining the current average loss value:

$$l_{current} = \text{sum}(\widetilde{\text{Queue}_i})/\text{len}(\widetilde{\text{Queue}_i})$$

where $\widetilde{\text{Queue}_i}$ is the loss queue after the unmanned aerial vehicle $c_i$ updates the local loss.

Further, specific steps of determining the communication quantization coefficient in S4 are as follows:

determining the communication quantization coefficient of r round communication round for the unmanned aerial vehicle $c_i$ by using $l_{history}$ and $l_{current}$;

$$q_i^r = \begin{cases} q_0, \text{ if } r = 1 \\ \sqrt{\frac{l_{history}}{l_{current}}}\, q_i^{r-1}, \text{ other} \end{cases}$$

where, r represents communication round of r round; when r=1 is selected, when the unmanned aerial vehicle $c_i$ is initially trained iteratively, due to absence of historical loss value in the loss queue, the historical average loss value $l_{history}$ fails to be calculated, so an initial quantization coefficient $q_0$ is given to determine an initial quantization level, $$q_i^{r-1}$$

is a communication quantization coefficient of the unmanned aerial vehicle $c_i$ in r−1 communication round.

However, due to the gradual convergence of the global model, it is not difficult to find that $$q_i^r$$

will increase obviously with the iteration of the number of communication rounds r, that is, the quantization effect is weakened compared with the quantization level of historical communication rounds. Therefore, the fading learning rate is further introduced to improve the shortcomings of the above mechanism and improve the problem that the quantization effect gradually weakens with the iteration of communication rounds. The revised quantization coefficient is:

$$\tilde{q}_i^r = \lceil \eta_l * q_i^r \rceil$$

where $\eta_l$ is unmanned aerial vehicle local learning rate decreasing slowly with training iteration.

Further, specific steps of random and uniform quantization in the S5 are as follows:

after determining quantization coefficient $$\tilde{q}_i^r$$

of the unmanned aerial vehicle $c_i$, compressing the model update by random and uniform quantization operation:

$$Q_{\tilde{q}_i^r}(\Delta w_i)=\|\Delta w\|_2 \operatorname{sign}(\Delta w_i)\zeta_i(\Delta w, \tilde{q}_i^r)$$

where $\Delta w_i$ is full-precision local model update of the unmanned aerial vehicle $c_i$, $\Delta w=[\Delta w_1, \ldots, \Delta w_d]$ is a parameter vector containing d dimensional model update, and random variable $$\zeta_i(\Delta w, \tilde{q}_i^r)$$

is determined by adaptive quantization coefficient $$\tilde{q}_i^r$$

$$\zeta_i(\Delta w, \tilde{q}_i^r)=\begin{cases}\frac{l+1}{\tilde{q}_i^r}, \text{ probability is } \frac{|\Delta\omega_i|}{\|\Delta w\|_2}\tilde{q}_i^r-1\\ \frac{l}{\tilde{q}_i^r}, \text{ other}\end{cases}$$

where $$l\in\{0, 1, 2, \ldots, \tilde{q}_i^r-1\}$$

is an integer variable satisfying $$\frac{|\Delta w_i|}{\|\Delta w\|_2}\in\left[\frac{l}{\tilde{q}_i^r}, \frac{l+1}{\tilde{q}_i^r}\right),$$

its significance is to ensure that the model update compression is within a reasonable quantization range. If unmanned aerial vehicle local update is 0, no quantization operation is performed, that is, if $$\Delta w_i=0, \text{ then } Q_{\tilde{q}_i^r}(\Delta w_i)=0;$$

after compressing the local model update $\Delta\tilde{w}_i$, transmitting and communicating $\Delta\tilde{w}_i$ to the central server, and preparing for next round communication after receiving the model update by the central server.

A reservoir area water bloom rapid monitoring device based on unmanned aerial vehicle swarm coordination includes a central server and unmanned aerial vehicles as clients; where reservoir area water bloom image data is collected by using unmanned aerial vehicle swarm.

Each of the unmanned aerial vehicles collects and saves the reservoir area water bloom image data, and a reservoir area water bloom rapid monitoring model is trained through federal learning algorithm; during r-th round of training, the central server sends r−1th round of global model update $\Delta\tilde{w}^{r-1}$ to N unmanned aerial vehicles;

the N unmanned aerial vehicles receiving global model update $\Delta\tilde{w}^{r-1}$ update a local model to $$w_i^r=w_i^{r-1}+\Delta\tilde{w}^{r-1},$$

where $$w_i^r$$

is a local model after updating $\Delta\tilde{w}^{r-1}$ and $$w_i^{r-1}$$

is a local model before updating $\Delta\tilde{w}^{r-1}$;

after updating the local model, unmanned aerial vehicles participating in federal training defines loss function queue according to water bloom image data collected by itself, and calculates a historical average loss value and a current average loss value;

the unmanned aerial vehicles use a ratio of historical loss function to current loss function to determine a communication quantization coefficient for the local model, and further introduces a fading learning rate to improve a problem of quantization effect gradually weakening with communication rounds iteration;

the unmanned aerial vehicles adopts random and uniform quantization operation to compress local model update, $\Delta\tilde{w}_i$ is quantized local model update of unmanned aerial vehicle $c_i$, and $\Delta\tilde{w}_i$ is transmitted and communicated to the central server; communication between the central server and the unmanned aerial vehicle swarm continues, so as to iteratively update the local model of the unmanned aerial vehicles and a global model of the central server until the global model converges or reaches a specified communication round; on a basis of ensuring accuracy of the global model, federal learning communication cost is greatly reduced, convergence speed of the reservoir area water bloom monitoring model is accelerated, and communication volume in a training process of the reservoir area water bloom monitoring model is greatly reduced, a final obtained global model is the reservoir area water bloom rapid monitoring model; in actual monitoring, a global model obtained by deployment is capable of being applied to newly collected image data to realize real-time water bloom monitoring; when new image data are collected, the new image data are sent to a deployed model for processing, and model outputs prediction results of whether water bloom exists in water body; the results are capable of being presented to users through visual interface or alarm system, thus monitoring personnel are helped to take timely measures to deal with water quality problems.

According to a reservoir area water bloom rapid monitoring method and device based on unmanned aerial vehicle swarm coordination, through the local updating quantification technology, on the basis of meeting the accuracy of the reservoir area water bloom monitoring model, with the goal of minimizing the communication volume during training, the reservoir area water bloom monitoring model is trained in combination with the UAV swarm. The reservoir area water bloom monitoring model is deployed on each UAV, which is used for online identification of water bloom sources in the reservoir area by UAV swarm, which is beneficial to rapid real-time identification and detection of water bloom sources in the reservoir area. The reservoir area water bloom rapid monitoring method and device based on unmanned aerial vehicle swarm coordination provided the disclosure accord with the realistic scene that unmanned aerial vehicles are weak in equipment capability and cannot undertake federal study of high communication volume, and provide a new method for jointly and rapidly training the reservoir area water bloom monitoring model by unmanned aerial vehicle swarm.

The specific implementation process and method of the device are the same, and will not be described in detail.

A computer device includes a memory, a processor and a computer program stored in the memory and capable of running on the processor, when the processor executes the computer program, a reservoir area water bloom rapid monitoring method based on unmanned aerial vehicle swarm coordination as above is realized.

A computer-readable storage medium is provided, where the computer-readable storage medium stores a computer program for executing a reservoir area water bloom rapid monitoring method based on unmanned aerial vehicle swarm coordination as above.

The beneficial effects are as follows: compare with the prior art, a reservoir area water bloom rapid monitoring method and device based on unmanned aerial vehicle swarm coordination are provided, through the local updating quantification technology, the communication volume between UAV and central server is compressed and the communication efficiency of federated learning is optimized on the premise of ensuring the accuracy of the reservoir area water bloom monitoring model. The local update quantification defines the loss function queue for UAV, and uses the ratio of historical and current loss functions to reasonably quantify the upstream model update. According to the disclosure, the problems that pictures collected by unmanned aerial vehicle swarm are difficult to upload in large quantities, the communication volume required for reservoir area water bloom monitoring is too large, and the reservoir area water bloom monitoring model converges slowly due to frequent communication are solved, the communication overhead between unmanned aerial vehicles and a central server is reduced, and the global model for water bloom monitoring in the reservoir area can be obtained more quickly.

BRIEF DESCRIPTION OF THE DRAWINGS

FIG. 1 is a method flow chart according to an embodiment of the disclosure.

DETAILED DESCRIPTION OF PREFERRED EMBODIMENTS

The disclosure will be further elucidated with reference to specific embodiments. It should be understood that these embodiments are only used to illustrate the disclosure and are not used to limit the scope of the disclosure. After reading the disclosure, various equivalent modifications of the disclosure by those skilled in the art fall within the scope defined by the appended claims of the disclosure.

The reservoir area water bloom rapid monitoring method based on unmanned aerial vehicle swarm coordination is provided, through local updating quantization technology, the communication volume between UAV and central server is compressed, which can greatly reduce the communication cost of federated learning on the basis of ensuring the accuracy of the global model, accelerate the convergence speed of the reservoir area water bloom monitoring model, and greatly reduce the communication volume in the training process of the reservoir area water bloom monitoring model.

As shown in FIG. 1, a reservoir area water bloom rapid monitoring method based on unmanned aerial vehicle swarm coordination is provided, and includes following steps:

S1: according to water bloom image data taken by the unmanned aerial vehicles, the local model (that is, the reservoir area water bloom rapid monitoring model) is trained through federal learning algorithm; in a training process of r-th round, r−1th round trained global model is updated $\Delta\tilde{w}^{r-1}$ and sent it to N unmanned aerial vehicles by the central server;

S2: the local model is updated to $$w_i^r = w_i^{r-1} + \Delta\tilde{w}^{r-1}$$

by the N unmanned aerial vehicles receiving global model update $\Delta\tilde{w}^{r-1}$, where $$w_i^r$$

is a local model after updating $\Delta\tilde{w}^{r-1}$ and $$w_i^{r-1}$$

is a local model before updating $\Delta\tilde{w}^{r-1}$;

S3: after updating the local model, an empty queue $Queue_i$ with a length of $\mu$ is defined by each of the unmanned aerial vehicles according to the water bloom image data collected by unmanned aerial vehicles participating in federal training, so as to store at most $\mu$ loss function values during local calculation of unmanned aerial vehicle $c_i$.

then, the historical average loss value is calculated by the unmanned aerial vehicles; where the historical average loss value refers to average loss stored in queue when the unmanned aerial vehicles fail to calculate current local loss:

$$l_{history} = \text{sum}(Queue_i)/\text{len}(Queue_i)$$

where sum($Queue_i$) is sum of loss values stored in queue of unmanned aerial vehicle $c_i$, and len($Queue_i$) is a queue length of $c_i$;

after the unmanned aerial vehicles obtain the historical average loss value $l_{history}$, local loss of current iterative training is calculated by the unmanned aerial vehicle $c_i$ and it is stored in training loss queue $Queue_i$; where before storing in the training loss queue, it is judged whether the training loss queue overflows, that is, whether a length of the training loss queue is equal to $\mu$; if equal, a first element is discharged in the training loss queue, and then updated loss is inserted; if not equal, a local loss value of the current iterative training is directly stored;

after updating the loss queue, the current average loss value is obtained:

$$l_{current} = \text{sum}(\widetilde{Queue_i})/\text{len}(\widetilde{Queue_i})$$

where $\widetilde{Queue_i}$ is the loss queue after the unmanned aerial vehicle $c_i$ updates the local loss.

S4: the communication quantization coefficient is determined for the local model by using the ratio of the historical loss function to the current loss function, and the fading learning rate is further introduced to improve the problem that the quantization effect gradually weakens with the iteration of communication rounds; the specific process is as follows:

the communication quantization coefficient of r round communication round is determined for the unmanned aerial vehicle $c_i$ by using $l_{history}$ and $l_{current}$;

$$q_i^r = \begin{cases} q_0, \text{ if } r = 1 \\ \sqrt{\frac{l_{history}}{l_{current}}}\, q_i^{r-1}, \text{ other} \end{cases}$$

where, r represents communication round of r round; when r=1 is selected, when the unmanned aerial vehicle $c_i$ is initially trained iteratively, due to absence of historical loss value in the loss queue, the historical average loss value $l_{history}$ fails to be calculated, so an initial quantization coefficient $q_0$ is given to determine an initial quantization level, $$q_i^{r-1}$$

is a communication quantization coefficient of the unmanned aerial vehicle $c_i$ in r−1 communication round.

However, due to the gradual convergence of the global model, it is not difficult to find that $$q_i^r$$

will increase obviously with the iteration of the number of communication find that rounds r, that is, the quantization effect is weakened compared with the quantization level of historical communication rounds. Therefore, the fading learning rate is further introduced to improve the shortcomings of the above mechanism and improve the problem that the quantization effect gradually weakens with the iteration of communication rounds. The revised quantization coefficient is:

$$\tilde{q}_i^r = \lceil \eta_l * q_i^r \rceil$$

where $\eta_l$ is unmanned aerial vehicle local learning rate decreasing slowly with training iteration.

S5: after determining quantization coefficient $$\tilde{q}_i^r$$

of the unmanned aerial vehicle $c_i$, the model update is compressed by random and uniform quantization operation:

$$Q_{\tilde{q}_i^r}(\Delta\omega_i) = \|\Delta w\|_2 \,\text{sign}(\Delta\omega_i)\, \zeta_i(\Delta w, \tilde{q}_i^r)$$

where $\Delta w_i$ is full-precision local model update of the unmanned aerial vehicle $c_i$, $\Delta w=[w_1, \ldots, \Delta w_d]$ is a parameter vector containing d dimensional model update, and random variable $$\zeta_i(\Delta w, \tilde{q}_i^r)$$

is determined by adaptive quantization coefficient $$\tilde{q}_i^r$$

$$\zeta_i(\Delta w, \tilde{q}_i^r) = \begin{cases} \frac{l+1}{\tilde{q}_i^r}, & \text{probability is } \frac{|\Delta\omega_i|}{\|\Delta w\|_2}\tilde{q}_i^r - 1 \\ \frac{1}{\tilde{q}_i^r}, & \text{other} \end{cases}$$

where $$l \in \{0, 1, 2, \ldots, \tilde{q}_i^r - 1\}$$

is an integer variable satisfying $$\frac{|\Delta\omega_i|}{\|\Delta w\|_2} \in \left[\frac{l}{\tilde{q}_i^r}, \frac{l+1}{\tilde{q}_i^r}\right),$$

its significance is to ensure that the model update compression is within a reasonable quantization range. If unmanned aerial vehicle local update is 0, no quantization operation is performed, that is, if $$\Delta w_i = 0, \text{ then } Q_{\tilde{q}_i^r}(\Delta w_i) = 0;$$

after compressing the local model update $\Delta\tilde{w}_i$, it is transmitted and communicated $\Delta\tilde{w}_i$ to the central server, and next round communication is prepared after receiving the model update by the central server.

S1-S5 are repeated until the global model converges or reaches a specified communication round, greatly reducing federal learning communication cost on a basis of ensuring accuracy of the global model, accelerating convergence speed of the reservoir area water bloom monitoring model, and greatly reducing communication volume in a training process of the reservoir area water bloom monitoring model. Each UAV collects and saves the reservoir area water bloom image data, and selects an appropriate machine learning model, such as deep learning convolutional neural network (CNN). Initialize the model on each device, and periodically aggregate the model parameters or gradients trained on each device to update the global model. The final obtained global model is the reservoir area water bloom rapid monitoring model. In actual monitoring, the obtained global model by deployment can be applied to newly collected image data to realize real-time water bloom monitoring. When new image data are collected, these data will be sent to the deployed model for processing, and the model will output the prediction results of whether there is water bloom in the water body. These results can be presented to users through visual interface or alarm system, these results helps monitoring personnel to take timely measures to deal with water quality problems.

A reservoir area water bloom rapid monitoring device based on unmanned aerial vehicle swarm coordination includes a central server and unmanned aerial vehicles as clients; where reservoir area water bloom image data is collected by using unmanned aerial vehicle swarm.

Each of the unmanned aerial vehicles collects and saves the reservoir area water bloom image data, and a reservoir area water bloom rapid monitoring model is trained through federal learning algorithm; during r-th round of training, the central server sends r−1th round of global model update $\Delta\tilde{w}^{r-1}$ to N unmanned aerial vehicles;

the N unmanned aerial vehicles receiving global model update $\Delta\tilde{w}^{r-1}$ update a local model to $$\omega_i^r = \omega_i^{r-1} + \Delta\tilde{\omega}^{r-1},$$

where $$\omega_i^r$$

is a local model after updating $\Delta\tilde{w}^{r-1}$ and $$\omega_i^{r-1}$$

is a local model before updating $\Delta\tilde{w}^{r-1}$;

after updating the local model, unmanned aerial vehicles participating in federal training defines loss function queue according to water bloom image data collected by itself, and calculates a historical average loss value and a current average loss value;

the unmanned aerial vehicles use a ratio of historical loss function to current loss function to determine a communication quantization coefficient for the local model, and further introduces a fading learning rate to improve a problem of quantization effect gradually weakening with communication rounds iteration;

the unmanned aerial vehicles adopts random and uniform quantization operation to compress local model update, $\Delta\tilde{w}_i$ is quantized local model update of unmanned aerial vehicle $c_i$, and $\Delta\tilde{w}_i$ is transmitted and communicated to the central server; communication between the central server and the unmanned aerial vehicle swarm continues, so as to iteratively update the local model of the unmanned aerial vehicles and a global model of the central server until the global model converges or reaches a specified communication round; on a basis of ensuring accuracy of the global model, federal learning communication cost is greatly reduced, convergence speed of the reservoir area water bloom monitoring model is accelerated, and communication volume in a training process of the reservoir area water bloom monitoring model is greatly reduced, a final obtained global model is the reservoir area water bloom rapid monitoring model; in actual monitoring, a global model obtained by deployment is capable of being applied to newly collected image data to realize real-time water bloom monitoring; when new image data are collected, the new image data are sent to a deployed model for processing, and model outputs prediction results of whether water bloom exists in water body; the results are capable of being presented to users through visual interface or alarm system, thus monitoring personnel are helped to take timely measures to deal with water quality problems.

Obviously, those skilled in the art should understand that the steps of the reservoir area water bloom rapid monitoring method based on unmanned aerial vehicle swarm coordination or the modules of the reservoir area water bloom rapid monitoring device based on unmanned aerial vehicle swarm coordination according to the embodiment of the disclosure described above can be realized by general computing devices, which can be concentrated on a single computing device or distributed on a network composed of multiple computing devices. Alternatively, they may be implemented by program codes executable by a computing device, so that they may be stored in a storage device for execution by the computing device. And in some cases, the steps shown or described may be performed in a different order from here, or they may be made into individual integrated circuit modules, or a plurality of modules or steps thereof may be made into a single integrated circuit module. Thus, embodiment of the disclosure are not limited to any particular combination of hardware and software.

What is claimed is:

1. A reservoir area water bloom rapid monitoring method based on unmanned aerial vehicle swarm coordination, compressing model update between unmanned aerial vehicles and a central server by local update quantification technology, collecting reservoir area water bloom image data by unmanned aerial vehicle swarm, and obtaining a global model by aggregating a local model trained on unmanned aerial vehicles, the global model being a reservoir area water bloom rapid monitoring model, wherein the method comprises following steps:

S1: according to water bloom image data taken by the unmanned aerial vehicles, training the local model by the unmanned aerial vehicles through federal learning algorithm, the local model is the reservoir area water bloom rapid monitoring model; in a training process of r-th round, updating r−1th round trained global model $\Delta\tilde{w}^{r-1}$ and sending to N unmanned aerial vehicles by the central server;

S2: updating the local model to $$\omega_i^r = \omega_i^{r-1} + \Delta\tilde{\omega}^{r-1}$$

by the N unmanned aerial vehicles receiving global model update $\Delta\tilde{w}^{r-1}$, wherein $$\omega_i^r$$

is a local model after updating $\Delta\tilde{w}^{r-1}$ and $$\omega_i^{r-1}$$

is a local model before updating $\Delta\tilde{w}^{r-1}$;

S3: after updating the local model, defining a loss function queue according to the water bloom image data collected by unmanned aerial vehicles participating in federal training, and calculating a historical average loss value and a current average loss value;

S4: determining a communication quantization coefficient for the local model by using a ratio of a historical loss function to a current loss function, and further introducing a fading learning rate to improve a problem of quantization effect gradually weakening with communication round iteration;

S5: compressing local model update $\Delta\tilde{w}_i$ by random and uniform quantization operation, wherein $\Delta\tilde{w}_i$ is quantized local model update of unmanned aerial vehicle $c_i$; transmitting and communicating $\Delta\tilde{w}_i$ to the central server; after receiving model update, preparing next round communication by the central server, and repeating S1-S5 until the global model converges or reaches a specified communication round, greatly reducing federal learning communication cost on a basis of ensuring accuracy of the global model, accelerating convergence speed of the reservoir area water bloom monitoring model, and greatly reducing communication volume in a training process of the reservoir area water bloom monitoring model, wherein a final obtained global model is the reservoir area water bloom rapid monitoring model.

2. The reservoir area water bloom rapid monitoring method based on unmanned aerial vehicle swarm coordination according to claim 1, wherein specific steps of calculating the historical average loss value and the current average loss value in the S3 are as follows:

defining an empty queue $Queue_i$ with a length of μ by each of the unmanned aerial vehicles, so as to store at most μ loss function values during local calculation of unmanned aerial vehicle $c_i$;

then, calculating the historical average loss value by the unmanned aerial vehicles; wherein the historical average loss value refers to average loss stored in queue when the unmanned aerial vehicles fail to calculate current local loss:

$$l_{history} = \text{sum}(\text{Queue}_i)/\text{len}(\text{Queue}_i)$$

wherein $\text{sum}(\text{Queue}_i)$ is sum of loss values stored in queue of unmanned aerial vehicle $c_i$, and $\text{len}(\text{Queue}_i)$ is a queue length of $c_i$;

after the unmanned aerial vehicles obtain the historical average loss value $l_{history}$, calculating local loss of current iterative training by the unmanned aerial vehicle $c_i$ and storing in training loss queue $Queue_i$; wherein before storing in the training loss queue, judging whether the training loss queue overflows, that is, whether a length of the training loss queue is equal to μ; if equal, discharging a first element in the training loss queue, and then inserting updated loss; if not equal, directly storing a local loss value of the current iterative training;

after updating the loss queue, obtaining the current average loss value:

$$l_{current} = \text{sum}(\widetilde{Queue_i})/\text{len}(\widetilde{Queue_i})$$

wherein $\widetilde{Queue_i}$ is the loss queue after the unmanned aerial vehicle $c_i$ updates the local loss.

3. The reservoir area water bloom rapid monitoring method based on unmanned aerial vehicle swarm coordination according to claim 1, wherein specific steps of determining the communication quantization coefficient in S4 are as follows:

determining the communication quantization coefficient of r round communication round for the unmanned aerial vehicle $c_i$ by using the historical average loss value $l_{history}$ and the current average loss value $l_{current}$;

$$q_i^r = \begin{cases} q_0, & \text{if } r = 1 \\ \sqrt{\dfrac{l_{history}}{l_{current}}}\, q_i^{r-1}, & \text{other} \end{cases}$$

wherein, r represents communication round of r round; when r=1 is selected, when the unmanned aerial vehicle $c_i$ is initially trained iteratively, due to absence of historical loss value in the loss queue, the historical average loss value $l_{history}$ fails to be calculated, so an initial quantization coefficient $q_0$ is given to determine an initial quantization level, $$q_i^{r-1}$$

is a communication quantization coefficient of the unmanned aerial vehicle $c_i$ in r−1 communication round.

4. The reservoir area water bloom rapid monitoring method based on unmanned aerial vehicle swarm coordination according to claim 3, introducing a fading learning rate to improve quantization effect, wherein a modified quantization coefficient is:

$$\tilde{q}_i^r = \lceil \eta_l * q_i^r \rceil$$

wherein $\eta_l$ is unmanned aerial vehicle local learning rate decreasing slowly with training iteration.

5. The reservoir area water bloom rapid monitoring method based on unmanned aerial vehicle swarm coordination according to claim 1, wherein specific steps of random and uniform quantization in the S5 are as follows:

after determining quantization coefficient $$\tilde{q}_i^r$$

of the unmanned aerial vehicle $c_i$, compressing the model update by random and uniform quantization operation:

$$Q_{\tilde{q}_i^r}(\triangle w_i)=\|\triangle w\|_2 \text{sign}(\triangle w_i)\zeta_i(\triangle w, \tilde{q}_i^r)$$

wherein $\Delta w_i$ is full-precision local model update of the unmanned aerial vehicle $c_i$, $\Delta w=[\Delta w_1, \ldots, \Delta w_d]$ is a parameter vector containing d dimensional model update, and random variable $$\zeta_i(\triangle w, \tilde{q}_i^r)$$

is determined by adaptive quantization coefficient $$\tilde{q}_i^r:$$

$$\zeta_i(\Delta w, \tilde{q}_i^r)=\begin{cases}\frac{l+1}{\tilde{q}_i^r}, \text{ probability is } \frac{|\Delta\omega_i|}{\|\Delta w\|_2}\tilde{q}_i^r - l \\ \frac{l}{\tilde{q}_i^r}, \text{ other}\end{cases}$$

wherein $$l \in \{0, 1, 2, \ldots, \tilde{q}_i^r - 1\}$$

is an integer variable satisfying $$\frac{|\triangle\omega_i|}{\|\triangle w\|_2} \in \left[\frac{l}{\tilde{q}_i^r}, \frac{l+1}{\tilde{q}_i^r}\right],$$

if unmanned aerial vehicle local update is 0, no quantization operation is performed, that is, if $$\Delta w_i = 0, \text{ then } Q_{\tilde{q}_i^r}(\Delta w_i) = 0,$$

after compressing the local model update $\Delta\tilde{w}_i$, transmitting and communicating $\Delta\tilde{w}_i$ to the central server, and preparing for next round communication after receiving the model update by the central server.

6. A non-transitory computer-readable storage medium, wherein the computer-readable storage medium stores a computer program for executing a reservoir area water bloom rapid monitoring method based on unmanned aerial vehicle swarm coordination according to claim 1.

7. A computer device, comprising a memory, a processor and a computer program stored in the memory and capable of running on the processor, wherein when the processor executes the computer program, a reservoir area water bloom rapid monitoring method based on unmanned aerial vehicle swarm coordination is realized, in the reservoir area water bloom rapid monitoring method based on unmanned aerial vehicle swarm coordination, compressing model update between unmanned aerial vehicles and a central server by local update quantification technology, collecting reservoir area water bloom image data by unmanned aerial vehicle swarm, and obtaining a global model by aggregating a local model trained on unmanned aerial vehicles, the global model being a reservoir area water bloom rapid monitoring model, wherein the method comprises following steps:

S1: according to water bloom image data taken by the unmanned aerial vehicles, training the local model by the unmanned aerial vehicles through federal learning algorithm, the local model is the reservoir area water bloom rapid monitoring model; in a training process of r-th round, updating r−1th round trained global model $\Delta\tilde{w}^{r-1}$ and sending to N unmanned aerial vehicles by the central server;

S2: updating the local model to $$w_i^r = w_i^{r-1} + \triangle\tilde{w}^{r-1}$$

by the N unmanned aerial vehicles receiving global model update $\Delta\tilde{w}^{r-1}$, wherein $$w_1^r$$

is a local model after updating $\Delta\tilde{w}^{r-1}$ and $$w_i^{r-1}$$

is a local model before updating $\Delta\tilde{w}^{r-1}$;

S3: after updating the local model, defining a loss function queue according to the water bloom image data collected by unmanned aerial vehicles participating in federal training, and calculating a historical average loss value and a current average loss value;

S4: determining a communication quantization coefficient for the local model by using a ratio of a historical loss function to a current loss function, and further introducing a fading learning rate to improve a problem of quantization effect gradually weakening with communication round iteration;

S5: compressing local model update $\Delta\tilde{w}_i$ by random and uniform quantization operation, wherein $\Delta\tilde{w}_i$ is quantized local model update of unmanned aerial vehicle $c_i$; transmitting and communicating $\Delta\tilde{w}_i$ to the central server; after receiving model update, preparing next round communication by the central server, and repeating S1-S5 until the global model converges or reaches a specified communication round, greatly reducing federal learning communication cost on a basis of ensuring accuracy of the global model, accelerating convergence speed of the reservoir area water bloom monitoring model, and greatly reducing communication volume in a training process of the reservoir area water bloom monitoring model, wherein a final obtained global model is the reservoir area water bloom rapid monitoring model.

8. The computer device according to claim 7, wherein specific steps of calculating the historical average loss value and the current average loss value in the S3 are as follows:

defining an empty queue $Queue_i$ with a length of μ by each of the unmanned aerial vehicles, so as to store at most μ loss function values during local calculation of unmanned aerial vehicle $c_i$;

then, calculating the historical average loss value by the unmanned aerial vehicles; wherein the historical average loss value refers to average loss stored in queue when the unmanned aerial vehicles fail to calculate current local loss:

$$l_{history} = \text{sum}(\text{Queue}_i)/len(\text{Queue}_i)$$

wherein $\text{sum}(\text{Queue}_i)$ is sum of loss values stored in queue of unmanned aerial vehicle $c_i$, and $\text{len}(\text{Queue}_i)$ is a queue length of $c_i$;

after the unmanned aerial vehicles obtain the historical average loss value $l_{history}$, calculating local loss of current iterative training by the unmanned aerial vehicle $c_i$ and storing in training loss queue $Queue_i$; wherein before storing in the training loss queue, judging whether the training loss queue overflows, that is, whether a length of the training loss queue is equal to μ; if equal, discharging a first element in the training loss queue, and then inserting updated loss; if not equal, directly storing a local loss value of the current iterative training;

after updating the loss queue, obtaining the current average loss value:

$$l_{current} = \text{sum}(\widetilde{Queue_i})/len(\widetilde{Queue_i})$$

wherein $\widetilde{Queue_i}$ is the loss queue after the unmanned aerial vehicle $c_i$ updates the local loss.

9. The computer device according to claim 7, wherein specific steps of determining the communication quantization coefficient in S4 are as follows:

determining the communication quantization coefficient of r round communication round for the unmanned aerial vehicle $c_i$ by using the historical average loss value $l_{history}$ and the current average loss value $l_{current}$;

$$q_i^r = \begin{cases} q_0, \text{ if } r = 1 \\ \sqrt{\dfrac{l_{history}}{l_{current}}}\, q_i^{r-1}, \text{ other} \end{cases}$$

wherein, r represents communication round of r round; when r=1 is selected, when the unmanned aerial vehicle $c_i$ is initially trained iteratively, due to absence of historical loss value in the loss queue, the historical average loss value $l_{history}$ fails to be calculated, so an initial quantization coefficient $q_0$ is given to determine an initial quantization level, $$q_i^{r-1}$$

is a communication quantization coefficient of the unmanned aerial vehicle $c_i$ in r−1 communication round.

10. The computer device according to claim 9, introducing a fading learning rate to improve quantization effect, wherein a modified quantization coefficient is:

$$\tilde{q}_i^r = \lceil \eta_l * q_i^r \rceil$$

wherein $\eta_l$ is unmanned aerial vehicle local learning rate decreasing slowly with training iteration.

11. The computer device according to claim 7, wherein specific steps of random and uniform quantization in the S5 are as follows:

after determining quantization coefficient $$\tilde{q}_i^r$$

of the unmanned aerial vehicle $c_i$, compressing the model update by random and uniform quantization operation:

$$Q_{\tilde{q}_i^r}(\Delta w_i) = \|\Delta w\|_2 \,\text{sign}(\Delta w_i)\zeta_i(\Delta w, \tilde{q}_i^r)$$

wherein $\Delta w_i$ full-precision local model update of the unmanned aerial vehicle $c_i$, $\Delta w=[\Delta w_1, \ldots, \Delta w_d]$ is a parameter vector containing d dimensional model update, and random variable $$\zeta_i(\Delta w, \tilde{q}_i^r)$$

is determined by adaptive quantization update, and random variable coefficient $$\tilde{q}_i^r$$

$$\zeta_i\left(\Delta w, \tilde{q}_i^r = \begin{cases} \dfrac{l+1}{\tilde{q}_i^r}, \text{ probability is } \dfrac{|\Delta\omega_i|}{\|\Delta w\|_2}\tilde{q}_i^r - l \\ \dfrac{1}{\tilde{q}_i^r}, \text{ other} \end{cases}\right.$$

wherein $$l \in \{0, 1, 2, \ldots, \tilde{q}_i^r - 1\}$$

is an integer variable satisfying $$\frac{|\Delta w_i|}{\|\Delta w\|_2} \in \left[\frac{l}{\tilde{q}_i^r}, \frac{l+1}{\tilde{q}_i^r}\right),$$

if unmanned aerial vehicle local update is 0, no quantization operation is performed, that is, if $$\Delta w_i = 0, \text{ then } Q_{q_i^r}(\Delta w_i) = 0;$$

after compressing the local model update $\Delta\tilde{w}_i$, transmitting and communicating $\Delta\tilde{w}_i$ to the central server, and preparing for next round communication after receiving the model update by the central server.

12. The computer device according to claim 7, wherein a reservoir area water bloom rapid monitoring device based on unmanned aerial vehicle swarm coordination is for performing the method, the reservoir area water bloom rapid monitoring device based on unmanned aerial vehicle swarm coordination comprises a central server and unmanned aerial vehicles as clients; wherein reservoir area water bloom image data is collected by using unmanned aerial vehicle swarm;

each of the unmanned aerial vehicles collects and saves the reservoir area water bloom image data, and a reservoir area water bloom rapid monitoring model is trained through federal learning algorithm; during r-th round of training, the central server sends r−1th round of global model update $\Delta\tilde{w}^{r-1}$ to N unmanned aerial vehicles;

the N unmanned aerial vehicles receiving global model update $\Delta\tilde{w}^{r-1}$ update a local model to $$w_i^r = w_i^{r-1} + \Delta\tilde{w}^{r-1},$$

wherein $$w_i^r$$

is a local model after updating $\Delta\tilde{w}^{r-1}$ and $$w_i^{r-1}$$

is a local model before updating $\Delta\tilde{w}^{r-1}$;

after updating the local model, unmanned aerial vehicles participating in federal training defines loss function queue according to water bloom image data collected by itself, and calculates a historical average loss value and a current average loss value;

the unmanned aerial vehicles use a ratio of historical loss function to current loss function to determine a communication quantization coefficient for the local model, and further introduces a fading learning rate to improve a problem of quantization effect gradually weakening with communication rounds iteration;

the unmanned aerial vehicles adopts random and uniform quantization operation to compress local model update, $\Delta\tilde{w}_i$ is quantized local model update of unmanned aerial vehicle $c_i$, and $\Delta\tilde{w}_i$ is transmitted and communicated to the central server, and the central server prepares for next round communication after receiving model update;

communication between the central server and the unmanned aerial vehicle swarm continues, so as to iteratively update the local model of the unmanned aerial vehicles and a global model of the central server until the global model converges or reaches a specified communication round; on a basis of ensuring accuracy of the global model, federal learning communication cost is greatly reduced, convergence speed of the reservoir area water bloom monitoring model is accelerated, and communication volume in a training process of the reservoir area water bloom monitoring model is greatly reduced, a final obtained global model is the reservoir area water bloom rapid monitoring model; in actual monitoring, a global model obtained by deployment is capable of being applied to newly collected image data to realize real-time water bloom monitoring; when new image data are collected, the new image data are sent to a deployed model for processing, and model outputs prediction results of whether water bloom exists in water body; the results are capable of being presented to users through visual interface or alarm system, thus monitoring personnel are helped to take timely measures to deal with water quality problems.

13. A reservoir area water bloom rapid monitoring device based on unmanned aerial vehicle swarm coordination, comprising a central server and unmanned aerial vehicles as clients; wherein reservoir area water bloom image data is collected by using unmanned aerial vehicle swarm;

each of the unmanned aerial vehicles collects and saves the reservoir area water bloom image data, and a reservoir area water bloom rapid monitoring model is trained through federal learning algorithm; during r-th round of training, the central server sends r−1th round of global model update $\Delta\tilde{w}^{r-1}$ to N unmanned aerial vehicles;

the N unmanned aerial vehicles receiving global model update $\Delta\tilde{w}^{r-1}$ update a local model to $$w_i^r = w_i^{r-1} + \Delta\tilde{w}^{r-1},$$

wherein $$w_i^r$$

is a local model after updating $\Delta\tilde{w}^{r-1}$ and $$w_i^{r-1}$$

is a local model before updating $\Delta\tilde{w}^{r-1}$;

after updating the local model, unmanned aerial vehicles participating in federal training defines loss function queue according to water bloom image data collected by itself, and calculates a historical average loss value and a current average loss value;

the unmanned aerial vehicles use a ratio of historical loss function to current loss function to determine a communication quantization coefficient for the local model, and further introduces a fading learning rate to improve a problem of quantization effect gradually weakening with communication rounds iteration;

the unmanned aerial vehicles adopts random and uniform quantization operation to compress local model update, is quantized local model update of unmanned aerial vehicle $c_i$, and $\Delta\tilde{w}_i$ is transmitted and communicated to the central server, and the central server prepares for next round communication after receiving model update; communication between the central server and the unmanned aerial vehicle swarm continues, so as to iteratively update the local model of the unmanned aerial vehicles and a global model of the central server until the global model converges or reaches a specified communication round; on a basis of ensuring accuracy of the global model, federal learning communication cost is greatly reduced, convergence speed of the reservoir area water bloom monitoring model is accelerated, and communication volume in a training process of the reservoir area water bloom monitoring model is greatly reduced, a final obtained global model is the reservoir area water bloom rapid monitoring model; in actual monitoring, a global model obtained by deployment is capable of being applied to newly collected image data to realize real-time water bloom monitoring; when new image data are collected, the new image data are sent to a deployed model for processing, and model outputs prediction results of whether water bloom exists in water body; the results are capable of being presented to users through visual interface or alarm system, thus monitoring personnel are helped to take timely measures to deal with water quality problems.

* * * * *